(12) United States Patent
Li et al.

(10) Patent No.: US 11,834,644 B2
(45) Date of Patent: Dec. 5, 2023

(54) PRESSURE BUFFERING SYSTEM AND BIOLOGICAL CULTURE DEVICE

(71) Applicant: Wistron Corporation, New Taipei (TW)

(72) Inventors: Ziya Li, New Taipei (TW); Huan-Chun Wu, New Taipei (TW); Chun-Chih Lai, New Taipei (TW)

(73) Assignee: Wistron Corporation, New Taipei (TW)

( * ) Notice: Subject to any disclaimer, the term of this patent is extended or adjusted under 35 U.S.C. 154(b) by 504 days.

(21) Appl. No.: 17/015,080

(22) Filed: Sep. 9, 2020

(65) Prior Publication Data
US 2021/0395669 A1 Dec. 23, 2021

(30) Foreign Application Priority Data
Jun. 19, 2020 (TW) .................. 109120758

(51) Int. Cl.
*C12M 1/34* (2006.01)
*C12M 1/32* (2006.01)
*C12M 1/00* (2006.01)
*C12M 1/12* (2006.01)

(52) U.S. Cl.
CPC ............ *C12M 41/40* (2013.01); *C12M 23/12* (2013.01); *C12M 23/38* (2013.01); *C12M 25/10* (2013.01); *C12M 29/24* (2013.01)

(58) Field of Classification Search
CPC ...... C12M 41/40; C12M 23/12; C12M 23/38; C12M 25/10; C12M 29/24
USPC ..................................................... 435/287.5
See application file for complete search history.

(56) References Cited

U.S. PATENT DOCUMENTS

| | | | |
|---|---|---|---|
| 6,271,027 B1* | 8/2001 | Sarem ................... | C12M 23/12 435/395 |
| 9,994,889 B2* | 6/2018 | Tipgunlakant ......... | C12M 23/16 |
| 10,570,934 B2 | 2/2020 | Kudo et al. | |
| 2016/0296858 A1 | 10/2016 | Hartmann et al. | |
| 2017/0298931 A1* | 10/2017 | Kudo .................. | F15B 15/1419 |
| 2018/0001265 A1 | 1/2018 | Hartmann et al. | |
| 2019/0308191 A1 | 10/2019 | Hart et al. | |

FOREIGN PATENT DOCUMENTS

| | | |
|---|---|---|
| CN | 107076178 | 8/2017 |
| CN | 107246933 | 10/2017 |
| CN | 107614080 | 1/2018 |
| JP | 2020089304 | 6/2020 |
| TW | 202012050 | 4/2020 |

OTHER PUBLICATIONS

Office Action of Taiwan Counterpart Application, dated Jan. 22, 2022, pp. 1-6.
"Office Action of Taiwan Counterpart Application", dated Nov. 11, 2020, with brief English summary thereof, p. 1-p. 8.
"Office Action of China Counterpart Application", dated Jun. 6, 2023, p. 1-p. 9.

* cited by examiner

*Primary Examiner* — Michael L Hobbs
*Assistant Examiner* — Lenora A Abel
(74) *Attorney, Agent, or Firm* — JCIPRNET

(57) ABSTRACT

A pressure buffering system includes a housing, a pump module, a pressure sensor and a pressure cylinder. The pump module, the pressure sensor and the pressure cylinder are disposed in the housing. The pressure cylinder is communicated between the pump module and the pressure sensor. A biological culture device is further provided.

18 Claims, 11 Drawing Sheets

PRESSURE BUFFERING SYSTEM AND BIOLOGICAL CULTURE DEVICE

CROSS-REFERENCE TO RELATED APPLICATION

This application claims the priority benefit of Taiwan application serial no. 109120758, filed on Jun. 19, 2020. The entirety of the above-mentioned patent application is hereby incorporated by reference herein and made a part of this specification.

BACKGROUND

1. Technical Field

The disclosure relates to a buffering system and a culture device, in particular to a pressure buffering system that offers a stable pressure and a biological culture device.

2. Description of Related Art

Generally speaking, when culturing cells in a well plate, cells and nutrient solution are placed in the grooves in the well plate. Since cells grow only in the two-dimensional direction (in the XY plane), the number of cells that can be cultured is limited by the cross-sectional area of the grooves of the well plate. To increase the number of cells that can be cultured, changes in gas pressure are now often used in the biomedical field to help cells grow in the Z direction.

FIG. 1A is a schematic diagram of a conventional pressure adjustment system. Referring to FIG. 1A, a cell and a nutrient solution are placed in a groove 14 of a well plate 13, and a cover 15 is disposed on the well plate 13. The cover 15 includes a gas opening 19 and multiple hollow tubes 16 communicated with the gas opening 19. A supply pump 10 and a vacuum pump 12 are respectively connected to the gas opening 19, and each hollow tube 16 extends into the corresponding groove 14 in the well plate 13 to divide the space in the groove 14 into an in-tube space 17 and an out-tube space 18. The in-tube space 17 and the out-tube space 18 are spaced apart from each other, but the pressure therein is communicated with each other, so the in-tube space 17 and the out-tube space 18 can be regarded as a communicating tube. Before the supply pump 10 and the vacuum pump 12 start to operate, a height H1 of the nutrient solution in the in-tube space 17 is equal to a height H1 of the nutrient solution in the out-tube space 18.

FIG. 1B is a schematic diagram of a vacuum pump of the pressure adjustment system of FIG. 1A during gas exhaustion. Referring to FIG. 1B, the vacuum pump 12 operates and exhausts the gas in the hollow tubes 16 to reduce the gas pressure in the hollow tubes 16. At this time, a height H2 of the nutrient solution in the in-tube space 17 increases, leading to a decrease of a height H3 of the nutrient solution in the out-tube space 18.

FIG. 1C is a diagram showing a relationship between time and pressure in an in-tube space when a vacuum pump of FIG. 1A is exhausting gas. Referring to FIG. 1C, in the present embodiment, an operator repeatedly makes the vacuum pump 12 stop after exhausting gas for five times. As can be seen in FIG. 1C, the pressure in the in-tube space 17 repeatedly drops and then rises for several times, making the nutrient solution and the cell in the in-tube space 17 and the nutrient solution and the cell in the out-tube space 18 to shake up and down and evenly mix in the height direction, thus increasing the speed of cell replication.

FIG. 1D is a schematic diagram of a supply pump of the pressure adjustment system of FIG. 1A during operation. Referring to FIG. 1D, during operation, the supply pump 10 sends gas into the hollow tubes 16 and increases the gas pressure in the hollow tubes 16. At this time, the nutrient solution in the in-tube space 17 is pushed down, and a height H4 of the nutrient solution in the in-tube space 17 is lowered, leading to an increase of a height H5 of the nutrient solution in the out-tube space 18.

FIG. 1E is a diagram showing a relationship between time and pressure in an in-tube space when a supply pump of FIG. 1A is operating. Referring to FIG. 1E, in the present embodiment, an operator repeatedly makes the supply pump 10 stop after operation for five times. As can be seen in FIG. 1C, the pressure in the in-tube space 17 repeatedly rises and then drops for several times, also making the nutrient solution and the cell in the in-tube space 17 and the nutrient solution and the cell in the out-tube space 18 to shake up and down and evenly mix in the height direction again, thus increasing the speed of cell replication.

However, in actual operation, the positive pressure and the negative pressure provided by the supply pump and the vacuum pump often vary too drastic, which may affect the rises and falls of the solution, resulting in turbulence flow and additional shearing force. FIG. 1F is a diagram showing a relationship between time and pressure in an in-tube space when a vacuum pump is actually operating. Referring to FIG. 1F, the system tries to maintain pressure so that the pressure varies within a range of −10 mm H2O plus or minus 10%, but as can be seen in FIG. 1F, the pressure largely exceeds the preset range (overshot). If the pressure is not accurately controlled, the cell cannot be cultured, and may even die from the additional shearing force produced in a flow field. Therefore, it is urgent to study how to stabilize the pressure within a desired small range of oscillation.

SUMMARY

A pressure buffering system of the disclosure provides a stable pressure.

In the disclosure, a pressure buffering system includes a housing, a pump module, a pressure sensor, and a pressure cylinder. The pump module, the pressure sensor, and the pressure cylinder are disposed in the housing. The pressure cylinder is communicated between the pump module and the pressure sensor.

In an embodiment of the disclosure, the pressure cylinder includes a first connector and a second connector. The first connector is connected to the pump module, and the second connector is communicated with the pressure sensor.

In an embodiment of the disclosure, an outer contour of the pressure cylinder includes two recessed notches, and the first connector and the second connector are located in the two recessed notches.

In an embodiment of the disclosure, the pressure buffering system further includes a valve, a conversion circuit, and a piezo pump control assembly. The valve is disposed between the pump module and the pressure cylinder, and the pump module includes a supply pump and a vacuum pump. The conversion circuit is electrically connected to the valve. The supply pump and the vacuum pump are two piezoelectric peristaltic pumps, and the piezo pump control assembly is electrically connected to the supply pump and the vacuum pump.

In an embodiment of the disclosure, the pressure buffering system further includes a controller, electrically connected to the piezo pump control assembly, the conversion circuit, and the pressure sensor.

In an embodiment of the disclosure, a power of the pump module is between 0.3 watts and 0.8 watts, and a volume of the pressure cylinder is between 5 ml and 15 ml.

In an embodiment of the disclosure, the outer contour of the pressure cylinder includes a flat surface, an arc surface, a curved surface, or a combination of at least two of the above.

A biological culture device of the disclosure includes a well plate, a cover, and a pressure buffering system. The cover is disposed on the well plate, and the pressure buffering system is connected to the cover and communicated with the well plate.

In an embodiment of the disclosure, the pressure buffering system includes a housing, a pump module, a pressure sensor, and a pressure cylinder. The pump module, the pressure sensor, and the pressure cylinder are disposed in the housing. The pressure cylinder is communicated between the pump module and the pressure sensor.

In an embodiment of the disclosure, the cover has a single gas opening, and the pump module and the pressure sensor are communicated with multiple grooves in the well plate through the gas opening.

In an embodiment of the disclosure, the cover includes multiple hollow tubes communicated with the gas opening, and each hollow tube extends into the corresponding groove to divide the space in the groove into an in-tube space and an out-tube space.

In an embodiment of the disclosure, the space in the groove is divided into the in-tube space and the out-tube space. The in-tube space and the out-tube space are communicated with each other, making the in-tube space and the out-tube space a communicating tube.

In an embodiment of the disclosure, the housing includes a first locator and the cover includes a second locator, and the first locator is aligned with the second locator.

In an embodiment of the disclosure, the well plate includes multiple grooves. The pressure buffering system is communicated with the grooves in the well plate.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1A:
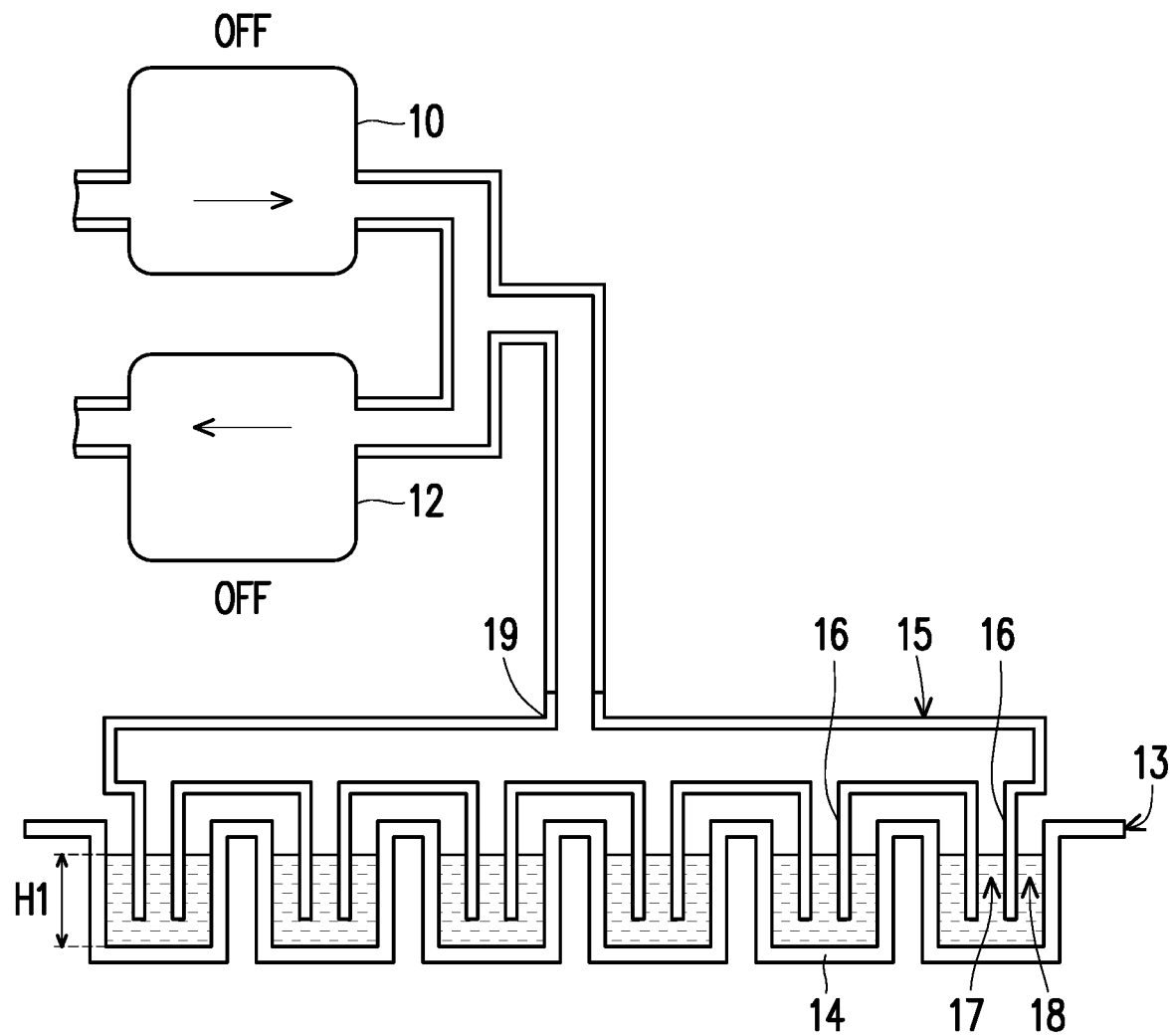
FIG. 1A is a schematic diagram of a conventional pressure adjustment system.
Figure 1B:
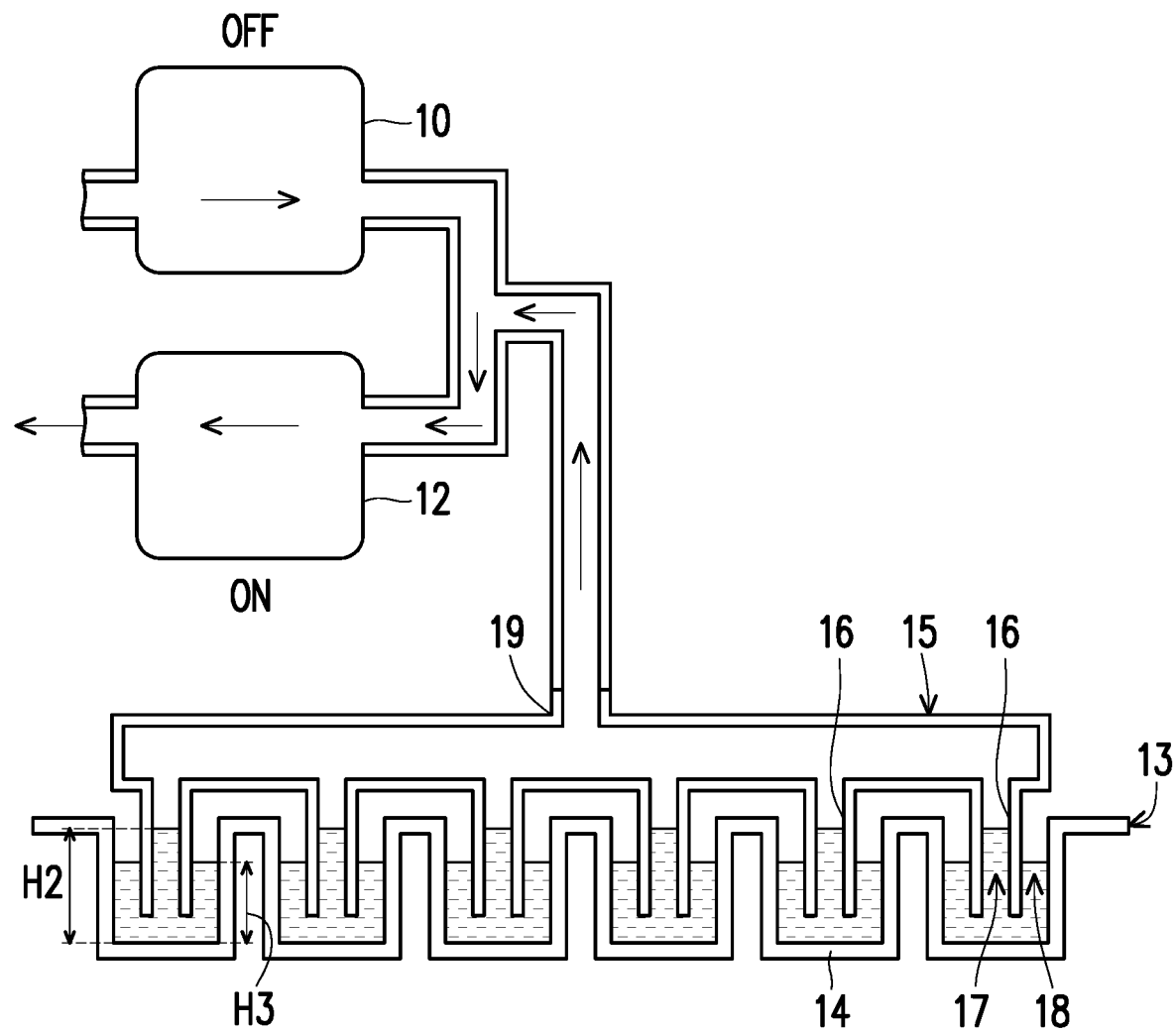
FIG. 1B is a schematic diagram of a vacuum pump of the pressure adjustment system of FIG. 1A during gas exhaustion.
Figure 1C:
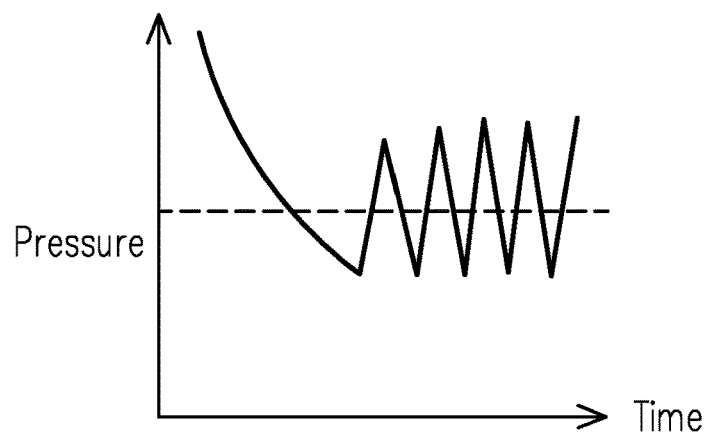
FIG. 1C is a diagram showing a relationship between time and pressure in an in-tube space when a vacuum pump of FIG. 1A is exhausting gas.
Figure 1D:
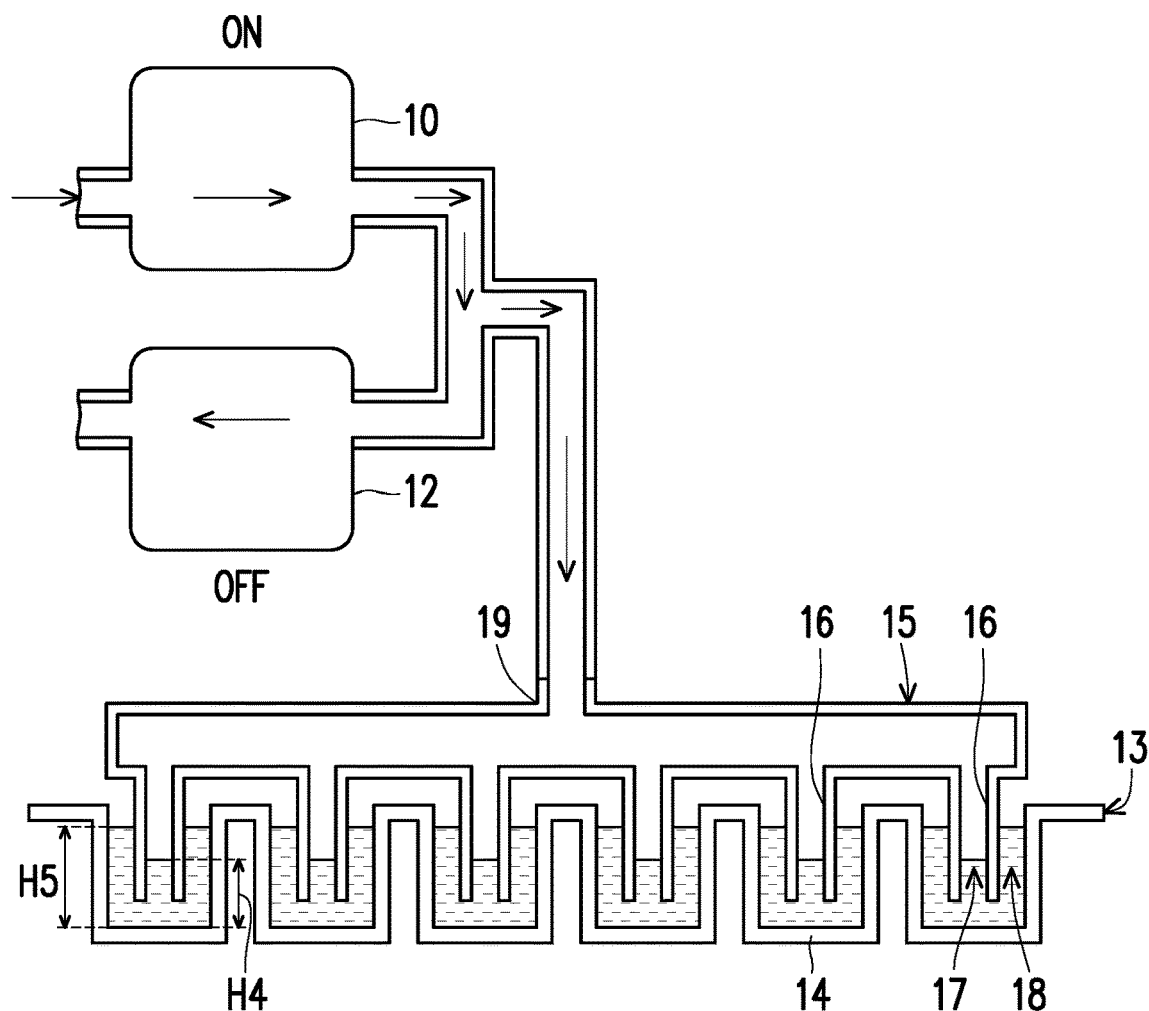
FIG. 1D is a schematic diagram of a supply pump of the pressure adjustment system of FIG. 1A during operation.
Figure 1E:
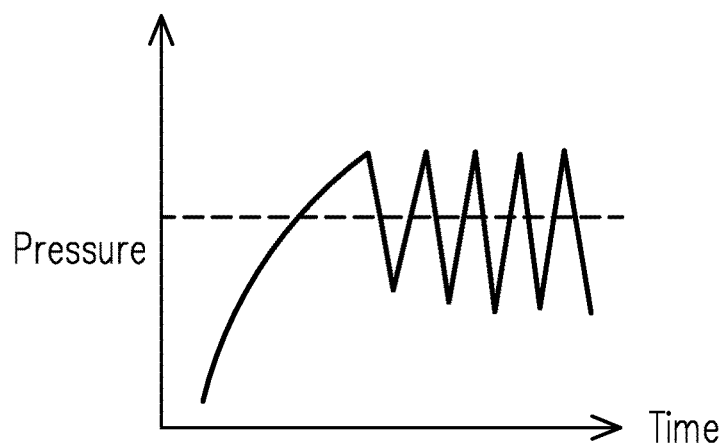
FIG. 1E is a diagram showing a relationship between time and pressure in an in-tube space when a supply pump of FIG. 1A is operating.
Figure 1F:
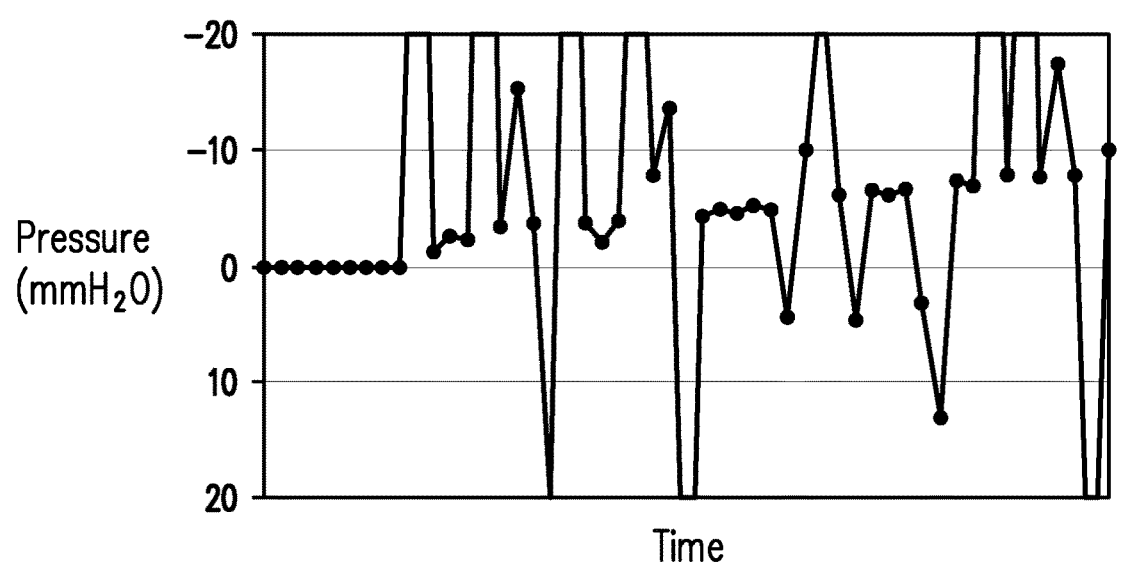
FIG. 1F is a diagram showing a relationship between time and pressure in an in-tube space when a vacuum pump is actually operating.

Reference will now be made in detail to the exemplary embodiments of the disclosure, examples of which are illustrated in the accompanying drawings. Wherever possible, the same reference numbers are used in the drawings and the description to refer to the same or like parts.

Figure 2A:
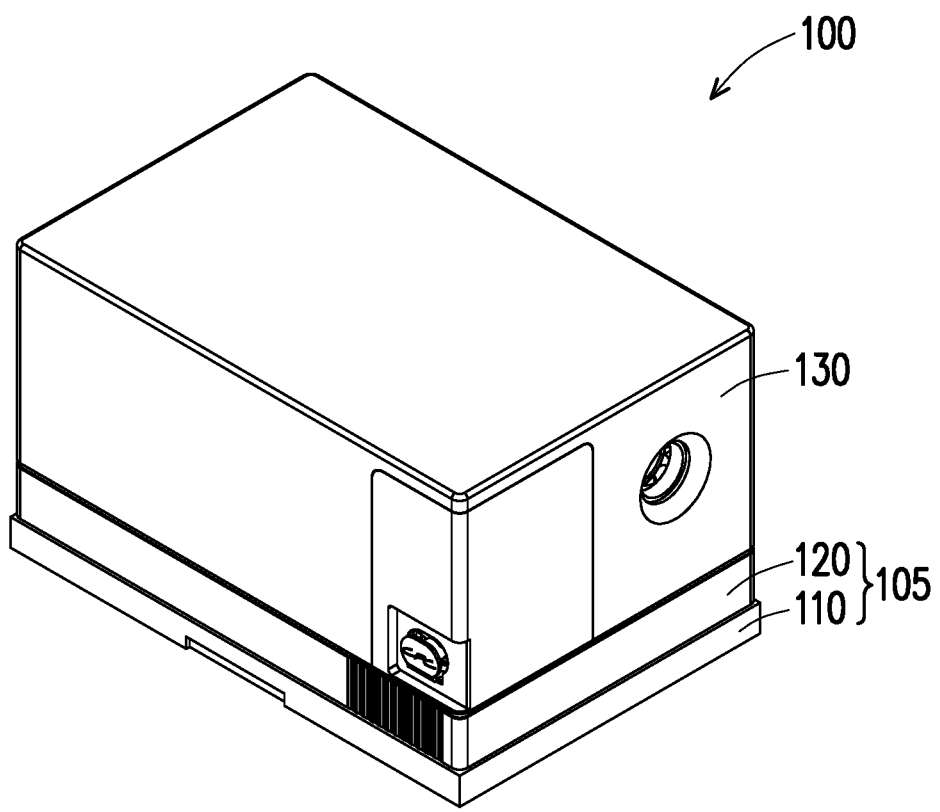
FIG. 2A is a schematic diagram of an appearance of a biological culture device according to an embodiment of the disclosure.
Figure 2B:
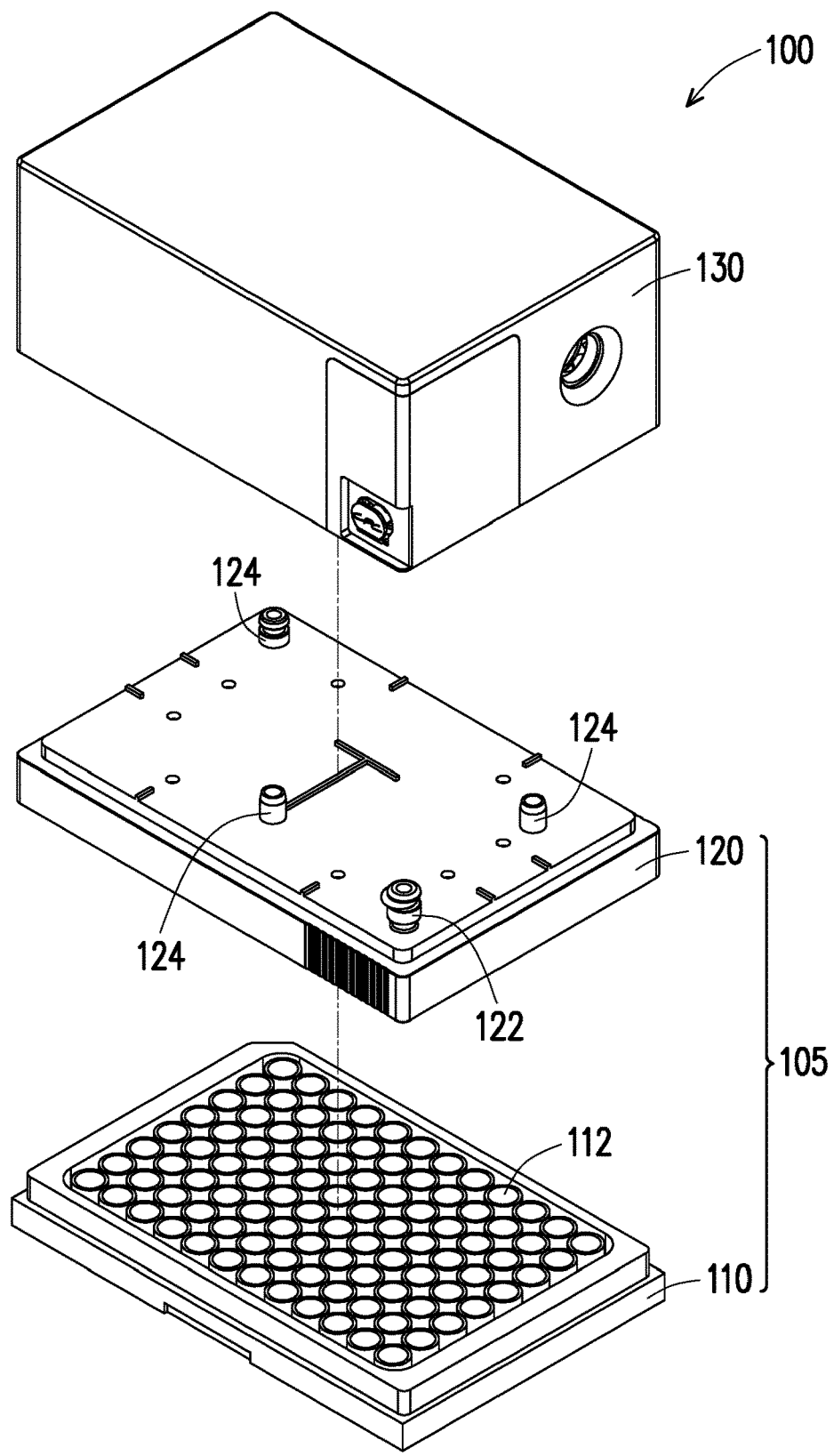
FIG. 2B is an exploded diagram of FIG. 2A.
Figure 2C:
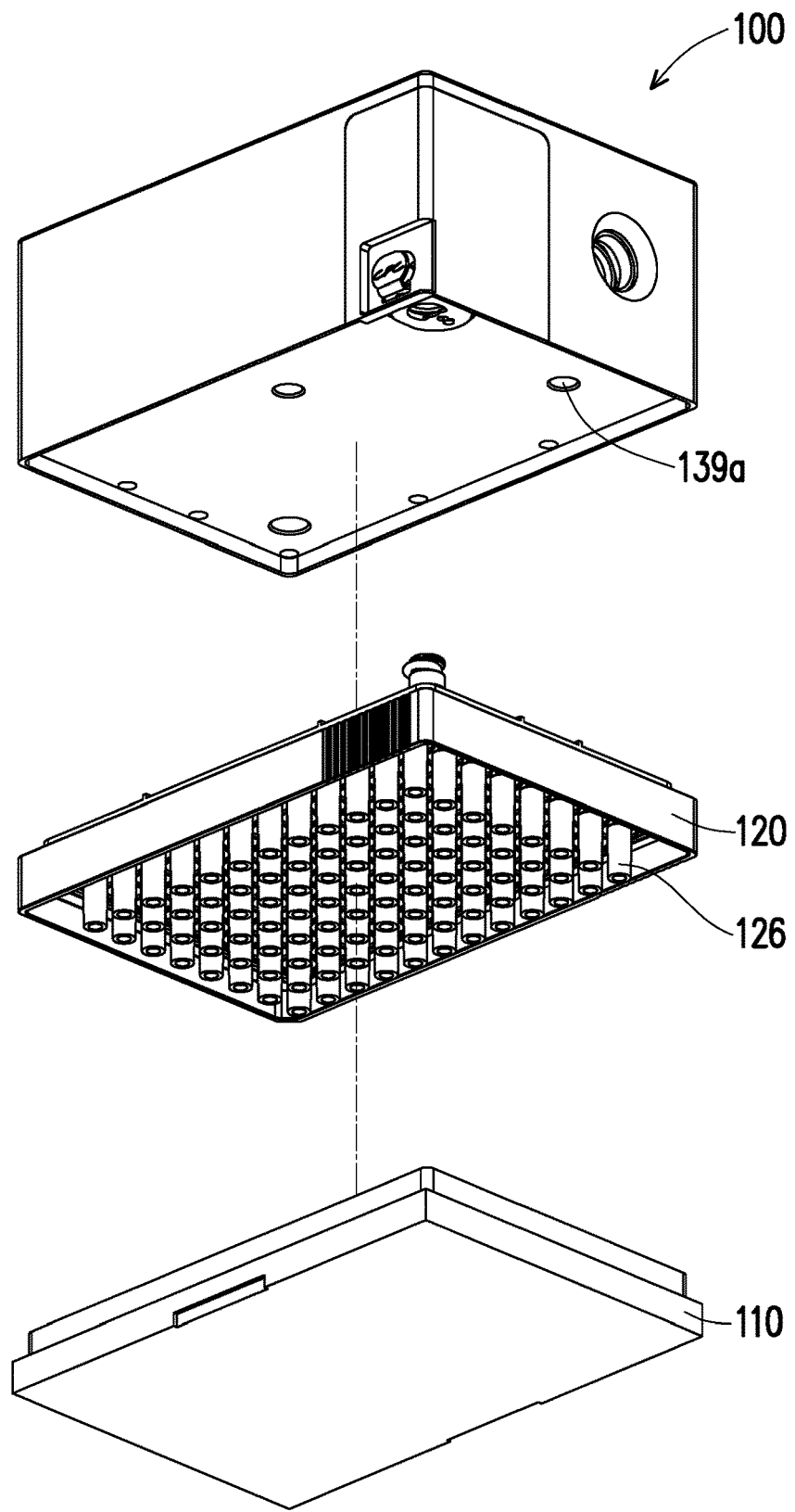
FIG. 2C is a schematic diagram of FIG. 2B from another perspective.

FIG. 2A is a schematic diagram of an appearance of a biological culture device according to an embodiment of the disclosure. FIG. 2B is an exploded diagram of FIG. 2A. FIG. 2C is a schematic diagram of FIG. 2B from another perspective.

In the present embodiment, a biological culture device 100 includes a well plate 110, a cover 120 disposed on the well plate 110, and a pressure buffering system 130. The pressure buffering system 130 is used to provide a stable pressure to a chamber 105. In the present embodiment, the well plate 110 and the cover 120 are provided in the chamber 105. Specifically, the chamber 105 is a chamber for cell culture. The well plate 110 includes multiple grooves 112. A gas opening 122 (shown in FIG. 2B) is located in the cover 120, and the cover 120 further includes multiple hollow tubes 126 communicated with the gas opening 122 (shown in FIG. 2C).

As shown in FIG. 2B and FIG. 2C, in the present embodiment, the chamber 105 has a single gas opening 122. The more the number of gas opening 122, the more likely leakage occurs; with a single gas opening 122, the possibility of leakage can be effectively reduced. A housing 139 includes a first locator 139a (shown in FIG. 2C), and the cover 120 includes a second locator 124 (shown FIG. 2B). The first locator 139a is aligned with the second locator 124, so that the pressure buffering system 130 and the chamber 105 can be well positioned with respect to each other. In the present embodiment, the second locator 124 is a projection and the first locator 139a is a recess. The second locator 124 may extend into the first locator 139a, so that the pressure buffering system 130 and the chamber 105 can be well positioned with respect to each other. Of course, in other embodiments, the second locator 124 may also be a recess and the first locator 139a may also be a projection, without being limited by the diagram.

Figure 3:
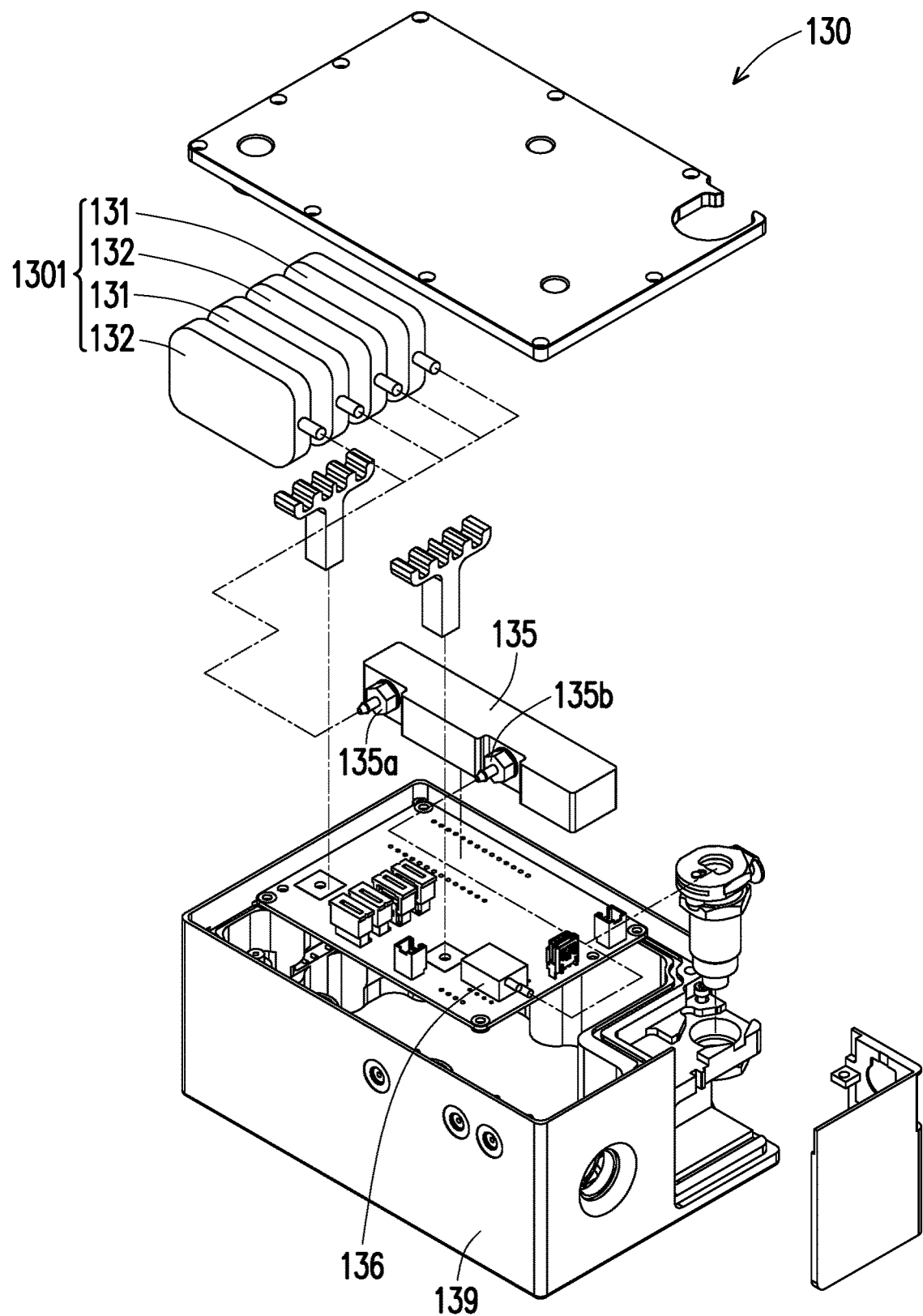
FIG. 3 is an exploded schematic diagram of a pressure buffering system of a biological culture device of FIG. 2A.

FIG. 3 is an exploded schematic diagram of a pressure buffering system of a biological culture device of FIG. 2A. Referring to FIG. 3, the pressure buffering system 130 includes the housing 139, a pump module 1301, a pressure sensor 136, and a pressure cylinder 135. The pump module 1301 includes at least one supply pump 131 and at least one vacuum pump 132. The supply pump 131, the vacuum pump 132, the pressure sensor 136, and the pressure cylinder 135 are located in the housing 139 and are protected by the housing 139. The supply pump 131 and the vacuum pump 132 are communicated with the chamber 105 through the gas opening 122 to pressurize the chamber 105 or to exhaust gas from the chamber 105.

The pressure cylinder 135 is disposed and communicated between the pump module 1301 and the pressure sensor 136. The pressure cylinder 135 includes a first connector 135a and a second connector 135b. The first connector 135a is connected to the supply pump 131 and the vacuum pump 132, and the second connector 135b is communicated with the pressure sensor 136 and the gas opening 122. Specifically, the pressure cylinder 135 is connected to the gas opening 122, and the pressure sensor 136 may sense the pressure value between the pressure cylinder 135 and the gas opening 122.

Therefore, when the supply pump 131 is in operation, the gas exhausted from the supply pump 131 flows through the pressure cylinder 135 and the gas opening 122 of the cover 120 to the chamber 105. When the vacuum pump 132 is in operation, the gas in the chamber 105 flows through the gas opening 122 of the cover 120 and the pressure cylinder 135 to the vacuum pump 132. With the design of the pressure cylinder 135 disposed between the pump module 1301 and the gas opening 122, the gas pressure can steadily enter and exit the chamber 105 and be accurately controlled.

The reason is that when the output power of the pump is a fixed value, the volume of the pressure cylinder 135 is inversely proportional to the pressure squared; by increasing the volume of the pressure cylinder 135, the velocity of the flow field can be reduced and the pressure can be stabilized more quickly. Based on the principle of conservation of energy, supposing that the energy of the pump at an output is represented by a linear term and an oscillating function $C1*\sin(t)$, the mass of the pressure cylinder 135 is m, and the energy output from the pressure cylinder 135 is represented by a linear term and an oscillating function $C2*\sin(t)$, since $C1/C2$ is proportional to the mass m, as has been proven by experiments, and C1 is a fixed value determined by the pump power, then the larger the mass m of the pressure cylinder 135, the smaller the C2. When C2 is smaller, the proportion of oscillation in the energy output from the pressure cylinder 135 is also smaller, thus pressure can be stabilized. Therefore, installing a pressure cylinder 135 with a certain volume in front of the pressure sensor 136 according to the output value of the pump module 1301 can help filter overshot problems.

It is worth mentioning that, in an embodiment, the larger the power P of the supply pump 131, the larger the volume V of the pressure cylinder 135. In the present embodiment, the power of the two supply pumps 131 is between 0.3 watts and 0.8 watts, for example, 0.5 watts; the power of the two vacuum pumps 132 is between 0.3 watts and 0.8 watts, for example, 0.5 watts; and the volume of the pressure cylinder 135 is between 5 ml and 15 ml, for example 10 ml. Of course, the power of the supply pump 131 and the vacuum pump 132 and the volume of the pressure cylinder 135 are not limited to the above-mentioned.

Moreover, in the present embodiment, the supply pump 131 and the vacuum pump 132 are two piezoelectric peristaltic pumps. The piezoelectric peristaltic pump uses piezoelectric materials to vibrate and pressurize, which may produce vibration frequency in itself during vibration that may affect the pressure sensor 136 and further affect the reading of the pressure sensor 136.

Generally speaking, to prevent the vibration frequency generated in the supply pump 131 and vacuum pump 132 from affecting the reading of the pressure sensor 136, additional connections are usually added so that the pressure sensor 136 is connected to the chamber 105 through other openings, but such arrangement may increase risk of airtight failure in the chamber 105.

In the present embodiment, the design that the pressure cylinder 135 is disposed between the pump module 1301 and the pressure sensor 136 can prevent the vibration frequency generated in the supply pump 131 and the vacuum pump 132 from affecting the reading of the pressure sensor 136, thereby improving the sensing accuracy of the pressure sensor 136.

In other words, installing the pressure cylinder 135 between the pump module 1301 and the pressure sensor 136 can help buffer the oscillation of the piezoelectric peristaltic pump. In this way, the pressure sensor 136 may not need to be connected to additional openings dug into the chamber 105 to avoid being affected by the supply pump 131 and the vacuum pump 132, and the chamber 105 can therefore maintain high airtightness. Of course, in other embodiments, the supply pump 131 and the vacuum pump 132 may also be piston pumps or screw pumps, or the like, and are not limited to piezoelectric peristaltic pumps.

Figure 4:
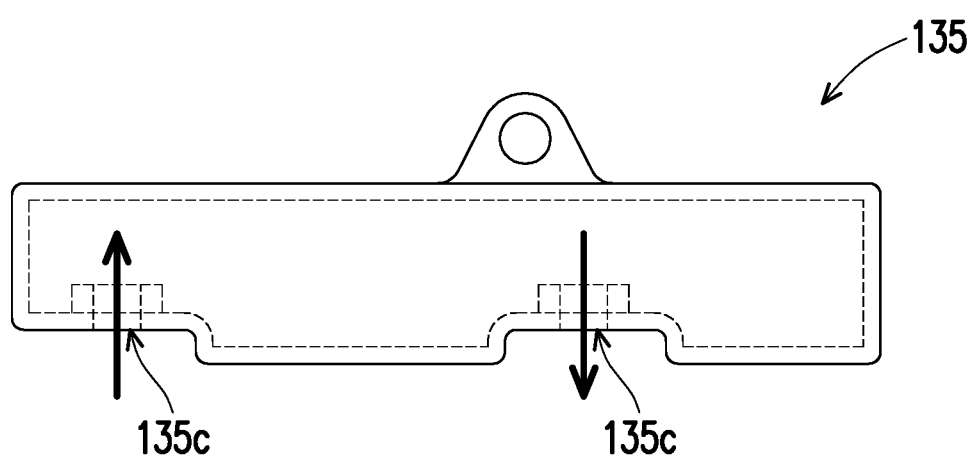
FIG. 4 is a schematic diagram of a pressure cylinder of FIG. 3.

FIG. 4 is a schematic diagram of a pressure cylinder of FIG. 3. Referring to FIG. 4, in the present embodiment, the outer contour of the pressure cylinder 135 includes two recessed notches 135c. The first connector 135a (shown in FIG. 3) and the second connector 135b (shown in FIG. 3) are located in the two notches 135c without protruding or only slightly protruding from the pressure cylinder 135 to protect the first connector 135a and the second connector 135b so that the two connectors are less likely to be hit directly.

It is worth mentioning that, in the present embodiment, the outer contour of the pressure cylinder 135 may correspond to the contours of other surrounding components to increase the size of the pressure cylinder 135 in a limited space. The outer contour of the pressure cylinder 135 includes a flat surface, an arc surface, a curved surface, or a combination of at least two of the above. A designer may determine the outer contour of the pressure cylinder 135 according to the convenience of manufacturing and the contour of the surrounding components.

Figure 5:
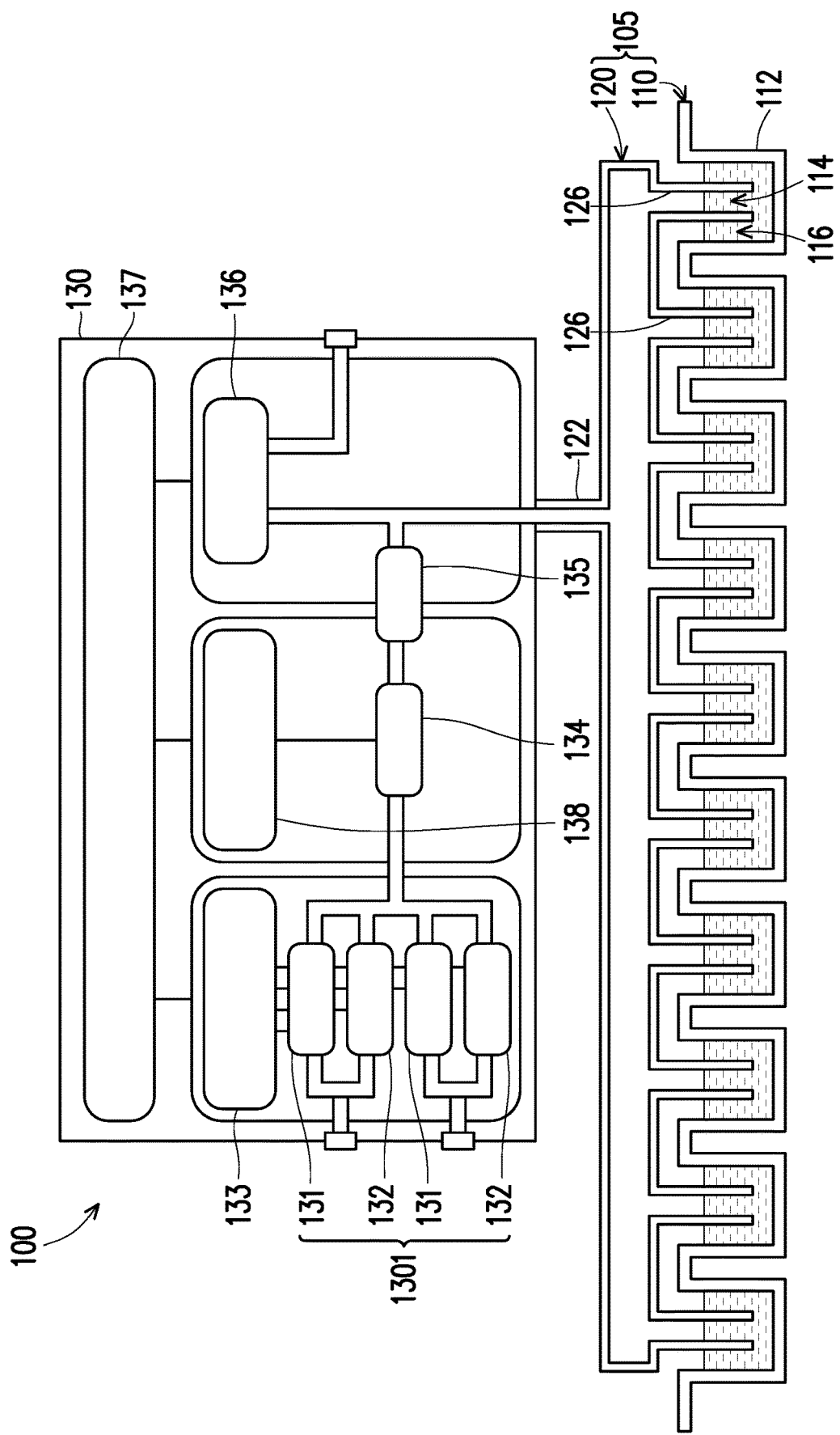
FIG. 5 is a schematic diagram of the biological culture device of FIG. 2A.

FIG. 5 is a schematic diagram of the biological culture device of FIG. 2A. Referring to FIG. 5, in the present embodiment, the pressure buffering system 130 further includes a controller 137, a piezo pump control assembly 133, a valve 134, and a conversion circuit 138. The controller 137 is electrically connected to the piezo pump control assembly 133, conversion circuit 138 and pressure sensor 136. The piezo pump control assembly 133 is electrically connected to the supply pump 131 and the vacuum pump 132.

The valve 134 is disposed between the pump module 1301 and the pressure cylinder 135. The valve 134 is used so that one of the supply pump 131 or the vacuum pump 132 is communicated with the chamber 105 and cut off the communication between the other one and the chamber 105. The conversion circuit 138 is electrically connected to the valve 134.

In the present embodiment, the controller 137 may control the piezo pump control assembly 133 to activate the supply pump 131 or the vacuum pump 132. The controller 137 may simultaneously control the conversion circuit 138 to determine whether the valve 134 allows the communication between the supply pump 131 and the pressure cylinder 135 or the communication between the vacuum pump 132 and the pressure cylinder 135. In addition, the controller 137 is electrically connected to the pressure sensor 136, so that the pressure sensor 136 may feedback the sensed information to the controller 137.

The pressure buffering system 130 is connected to the gas opening 122 of the cover 120, and each hollow tube 126 of the cover 120 extends into the corresponding groove 112 to divide the space in the groove 112 into an in-tube space 114 and an out-tube space 116. The in-tube space 114 and the out-tube space 116 may be regarded as a communicating tube so as to change the liquid level in the in-tube space 114 and the out-tube space 116 according to the pressure input or output by the pressure buffering system 130 to facilitate mixing of the cell and the nutrient solution.

Figure 6:
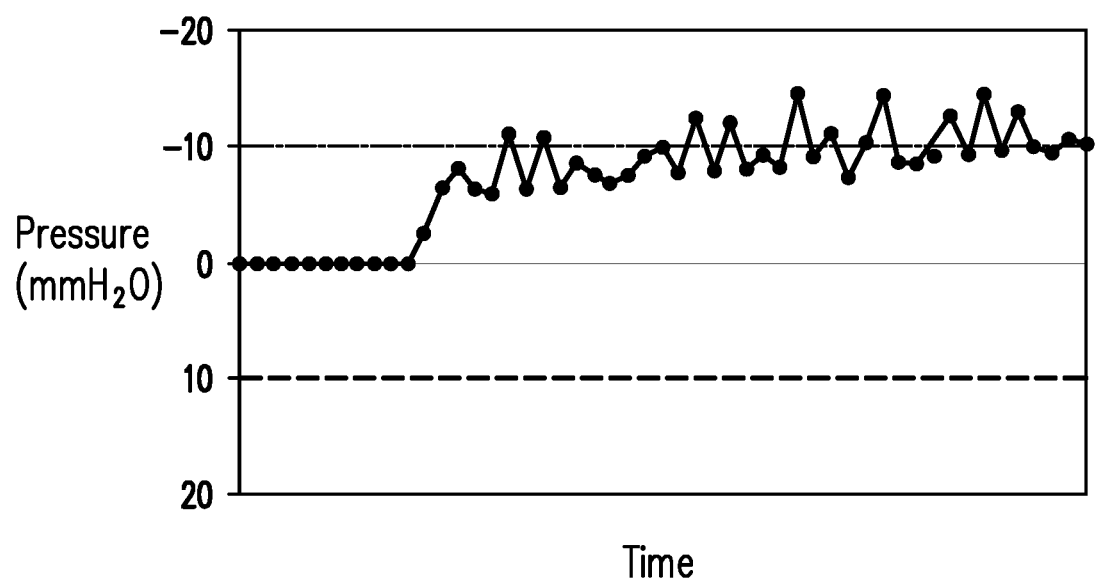
FIG. 6 is a diagram showing a relationship between time and pressure in an in-tube space when a vacuum pump of FIG. 2A is operating.

FIG. 6 is a diagram showing a relationship between time and pressure in an in-tube space when a vacuum pump of FIG. 2A is operating. Referring to FIG. 6, the operation mode of the vacuum pump 132 is set to be reduced from 10 mm H2O to −10 mm H2O; when the pressure of the in-tube space 114 exceeds 10% of −10 mm H2O, the vacuum pump 132 is turned off, and when the pressure of the in-tube space 114 is lower than 10% of −10 mm H2O, the vacuum pump 132 is turned on. As can be clearly seen in FIG. 6, the pressure can be accurately controlled within a certain range without excessive oscillation.

In other words, in the present embodiment, the biological culture device 100 is provided with a pressure cylinder 135 disposed between the pump module 1301 and the pressure sensor 136 so as to effectively buffer the oscillation between the pressure cylinder 135 and the gas opening 122, thereby providing a stable pressure. In addition, the above design also helps reduce the vibration impact on the pressure sensor 136, allowing the pressure sensor 136 to maintain high accuracy. In this way, the biological culture device 100 can still obtain good feedback under the condition that the chamber 105 maintains a single gas opening 122.

In summary, in the disclosure, the pressure buffering system provides a stable pressure by including a pressure cylinder communicated between the pump module and the pressure sensor to facilitate accurate control. By the design of the biological culture device, the pressure buffering system of the disclosure provides a stable pressure to the well plate, allowing the pressure to steadily fluctuate within a desired small range, which can effectively prevent the pressure from largely exceeding the preset range and avoid failure in cell culturing.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A pressure buffering system, comprising:
    a housing;
    a pump module, disposed in the housing;
    a pressure sensor, disposed in the housing; and
    a pressure cylinder, disposed in the housing and communicated between the pump module and the pressure sensor, wherein the pressure cylinder stabilizes a pressure of a gas entering or exiting the housing.

2. The pressure buffering system according to claim 1, wherein the pressure cylinder comprises a first connector and a second connector, the first connector is connected to the pump module, and the second connector is communicated with the pressure sensor.

3. The pressure buffering system according to claim 2, wherein an outer contour of the pressure cylinder comprises two recessed notches, and the first connector and the second connector are located in the two notches.

4. The pressure buffering system according to claim 1, wherein an outer contour of the pressure cylinder comprises a flat surface, an arc surface, a curved surface, or a combination of at least two of the above.

5. The pressure buffering system according to claim 1, further comprising:
    a valve, disposed between the pump module and the pressure cylinder, wherein the pump module comprises a supply pump and a vacuum pump;
    a conversion circuit, electrically connected to the valve; and
    a piezo pump control assembly, wherein the supply pump and the vacuum pump are two piezoelectric peristaltic pumps, and the piezo pump control assembly is electrically connected to the supply pump and the vacuum pump.

6. The pressure buffering system according to claim 5, further comprising:
    a controller, electrically connected to the piezo pump control assembly, the conversion circuit, and the pressure sensor.

7. The pressure buffering system according to claim 1, wherein a power of the pump module is between 0.3 watts and 0.8 watts, and a volume of the pressure cylinder is between 5 ml and 15 ml.

8. A biological culture device, comprising:
    a well plate;
    a cover, disposed on the well plate, wherein a single gas opening is disposed in the cover; and
    a pressure buffering system, connected to the cover and communicated with the well plate through the gas opening, wherein the pressure buffering system stabilizes a gas pressure and provides the gas pressure to the well plate.

9. The biological culture device according to claim 8, wherein the pressure buffering system comprises:
    a housing;
    a pump module, disposed in the housing;
    a pressure sensor, disposed in the housing; and
    a pressure cylinder, disposed in the housing and communicated between the pump module and the pressure sensor.

10. The biological culture device according to claim 9, wherein the pump module and the pressure sensor are communicated with a plurality of grooves in the well plate through the gas opening.

11. The biological culture device according to claim 10, wherein the cover comprises a plurality of hollow tubes communicated with the gas opening, and each hollow tube extends into the corresponding groove.

12. The biological culture device according to claim 11, wherein a space in the groove is divided into an in-tube space and an out-tube space, and the in-tube space and the out-tube space are communicated with each other, making the in-tube space and the out-tube space a communicating tube.

13. The biological culture device according to claim 9, wherein the housing comprises a first locator and the cover comprises a second locator, and the first locator is aligned with the second locator.

14. The biological culture device according to claim 9, wherein the pressure cylinder comprises a first connector and a second connector, the first connector is connected to the pump module, and the second connector is communicated with the pressure sensor.

15. The biological culture device according to claim 14, wherein an outer contour of the pressure cylinder comprises two recessed notches, and the first connector and the second connector are located in the two notches.

16. The biological culture device according to claim 9, wherein an outer contour of the pressure cylinder comprises a flat surface, an arc surface, a curved surface, or a combination of at least two of the above.

17. The biological culture device according to claim 9, wherein a power of the pump module is between 0.3 watts and 0.8 watts, and a volume of the pressure cylinder is between 5 ml and 15 ml.

18. The biological culture device according to claim 8, wherein the well plate comprises a plurality of grooves, and the pressure buffering system is communicated with the grooves in the well plate.

\* \* \* \* \*